United States Patent
Miyagawa

(10) Patent No.: US 7,619,212 B2
(45) Date of Patent: Nov. 17, 2009

(54) CHROMATOGRAPHIC ANALYZER

(75) Inventor: Haruhiko Miyagawa, Kyoto (JP)

(73) Assignee: Shimadzu Corporation, Kyoto-fu (JP)

( * ) Notice: Subject to any disclaimer, the term of this patent is extended or adjusted under 35 U.S.C. 154(b) by 275 days.

(21) Appl. No.: 11/599,402

(22) Filed: Nov. 15, 2006

(65) Prior Publication Data

US 2008/0110232 A1    May 15, 2008

(51) Int. Cl.
*B01D 59/44*    (2006.01)
*H01J 49/00*    (2006.01)
(52) U.S. Cl. .................. 250/282; 250/281; 250/284
(58) Field of Classification Search .......... 250/284, 250/288, 282
See application file for complete search history.

(56) References Cited

U.S. PATENT DOCUMENTS 5,453,613 A * 9/1995 Gray et al. .............. 250/281
6,006,584 A 12/1999 Itoi
6,573,496 B2 * 6/2003 Harada ..................... 250/293

FOREIGN PATENT DOCUMENTS

JP    10-283982 A    10/1998

* cited by examiner

*Primary Examiner*—David A Vanore
(74) *Attorney, Agent, or Firm*—Sughrue Mion, PLLC

(57) ABSTRACT

When a standard specimen including a given reference component is analyzed after a separation condition is changed, a data processing section (31) acquires an actual measurement value of a peak of a reference component that appears in a chromatogram obtained by the analysis, and estimates a deviation of the retention time of a peak of an intended component on the basis of the actual measurement value and information on the retention time of the reference component before the separation condition stored in an analysis condition information storing section (34) is changed, to correct a measurement time range of the respective ion sets of an SIM measurement parameter which is stored in an analysis condition information storing section (34). An SIM measurement is conducted according to the parameter that is corrected when analyzing the intended specimen, to thereby make it possible to conduct a desired measurement by an operator.

1 Claim, 3 Drawing Sheets

Fig. 4

| ION SET | START (MIN) | END (MIN) | MEASUREMENT MASS NUMBER 1 | MEASUREMENT MASS NUMBER 2 | MEASUREMENT MASS NUMBER 3 |
|---|---|---|---|---|---|
| 1 | 10 | 11 | 100 | 110 | 120 |
| 2 | 11 | 12 | 200 | 210 | 220 |
| 3 | 13 | 14 | 300 | 310 | 320 |

Fig. 5

| ION SET | START (MIN) | END (MIN) | MEASUREMENT MASS NUMBER 1 | MEASUREMENT MASS NUMBER 2 | MEASUREMENT MASS NUMBER 3 |
|---|---|---|---|---|---|
| 1 | Ts'[1] | Te'[1] | 100 | 110 | 120 |
| 2 | Ts'[2] | Te'[2] | 200 | 210 | 220 |
| 3 | Ts'[3] | Te'[3] | 300 | 310 | 320 |

CHROMATOGRAPHIC ANALYZER

BACKGROUND OF THE INVENTION

1. Field of the Invention

The present invention relates to a chromatographic analyzer such as a gas chromatograph (GC), a liquid chromatograph (LC), or a chromatograph mass spectrometer (GC/MS or LC/MS) obtained by combination of such the chromatograph with a mass spectrometer (MS).

2. Description of the Related Art

In a chromatographic analysis using a separation column, an analysis condition according to characteristics of the column is set prior to the analysis of an intended specimen, and the analysis is automatically performed according to the analysis condition. In general, a standard specimen containing a compound to be analyzed is actually analyzed, and an optimum analysis condition is set on the basis of the analysis result. Hereinafter, a gas chromatograph mass spectrometer (GC/MS) obtained by combination of the gas chromatograph (GC) with the mass spectrometer (MS) will be described as an example.

As a data collecting method in the MS section of the GC/MS, there have been known a so-called scanning measurement and a selected ion monitoring (SIM) measurement, and any one of those measurements is selected as usual (for example, refer to JP 10-283982 A). In the scanning measurement, since the repetitive mass number is scanned within a given mass number range, all of ions that are contained within the mass number range are detected. Therefore, the scanning measurement is useful for a case in which the mass number of a component to be analyzed is unknown, including the qualitative analysis of an unknown specimen. On the other hand, in the SIM measurement, only ions having one or more specific mass numbers designated in advance are selectively detected in a time division fashion. Therefore, the SIM measurement is useful for a case in which a material to be analyzed is known, and the quantitative analysis of the material is conducted with a high sensitivity.

As the data collection conditions (i.e., scanning measurement parameters) in a case of conducting the scanning measurement, it is necessary to set a measurement start time and a measurement end time together with the mass number range to be measured. For example, in a case where the mass number range is set to 100 to 500, the measurement start time is set to 5 minutes, and the measurement end time is set to 18 minutes, a time point at which the specimen is injected into a specimen gasifying chamber that is provided at a column inlet is set as zero, the mass number range of 100 to 500 is repeated with a given mass number step width, and the detected data is collected while performing mass scanning for 13 minutes, from a time point at which 5 minutes elapse to a time point at which 18 minutes elapse.

On the other hand, as the data collection conditions (i.e., SIM measurement parameter) in a case of conducting the SIM measurement, it is necessary to set one or more mass numbers to be measured as well as the measurement start time and the measurement end time. However, in general, the different mass numbers are measured according to the eluting times of various components from the column, so a plurality of measurement time ranges that are regulated by the measurement start time and the measurement end time can be set. For example, The measurement time range: 5 to 8 minutes, the measurement mass number: 151, 120, and 130.

The measurement time range: 8 to 10 minutes, the measurement mass number: 250, 273, 157, 311, 256, and 450.

The measurement time range: 10 to 12 minutes, the measurement mass number: 167, 345, and 327.

Thus, the measurement time range is sectioned, and one or more measurement mass numbers are set for each of the measurement time ranges. At the time of executing the analysis, in the MS section, the detected data is collected while sequentially switching over the mass number to be measured with a time elapse from the specimen injection time point according to the setting contents. In this specification, one measurement time range of the SIM measurement is called "ion set". That is, in the above example, three ion sets are set.

Incidentally, in the gas chromatograph, a time when the peak of the same component appears on the chromatogram is varied due to various factors. For example, the time is varied in a case of cutting an inlet portion of a capillary column by a given length in order to maintain the capillary column, in a case of changing a temperature rising program of a column oven that is one of the analysis conditions, or in a case where the column is exchanged to a column that is different in size such as the inner diameter or the length.

In the GC/MS, in a case where there is a factor that causes a variation of the chromatogram in the time axial direction, it is necessary to change the above data collection conditions that nave been set in advance (specifically, temporal parameter such as the above measurement time range). In the case of the scanning measurement, it is only necessary to change the two temporal parameters of the measurement start time and the measurement end time. However, in a case of the SIM measurement, all of the measurement start time and the measurement end time of the respective ion sets must be changed. In the existing GC/MS, the number of maximum ion sets that can be set is larger, specifically for example, 32, 64, or more, and in a case of setting a large number of ion sets, the change of the temporal parameter as described above is a significantly laborious work for an operator.

Also, in the GC/MS, there is a case in which a measurement that combines the scanning measurement with the SIM measurement, or the MS/MS (MSn) analysis is conducted. Even in this measurement, it is necessary to set various parameters every time the compound is eluted from the column, so when the chromatogram is varied in the time axial direction as described above, those parameters must be also changed. Also, the changing operation is significantly troublesome and laborious in a case where there are many compounds to be measured.

Further, there arises the same problem not in the GC/MS but in a case of executing a process that depends on the processing condition including the temporal parameter, for example, fractionating and sorting the specimen component that is temporally separated by the column as with the preparative liquid chromatograph. Even in this case, the changing operation of the processing conditions is troublesome, for example, when the number of specimen components to be fractionated and sorted is large.

SUMMARY OF THE INVENTION

The present invention has been made to solve the above-mentioned problems, and therefore an abject of the present invention is to provide a chromatographic analyzer which is capable of reducing a load on an operator or an operation error by simply changing data collection conditions or processing conditions which have been already set in a case where there is a factor that causes a chromatogram to vary in a time axial direction, such as cutoff of an inlet end of a capillary column.

Up to now, in order to accurately identify a peak of an unknown component that appears in the chromatogram which has been acquired by chromatographically analyzing a certain specimen, the following data processing have been conducted. That is, a retention time of the peak of the unknown component is corrected on the basis of an actual measurement retention time of the peak of the known component, and the corrected retention time is subjected to a peak identification with reference to qualitative database, or the retention time that is recorded in the qualitative database is corrected, and the corrected value is used to perform the peak identification. In other words, after the chromatogram data has been acquired, a variation of the chromatogram in the time axial direction with respect to the acquired data is corrected, or a variation of the chromatogram in the time axial direction is corrected with respect to an analysis parameter for identifying the data.

The conventional correction is conducted after the analysis of the intended specimen has been executed. The present invention achieves the above-mentioned object by applying such the correction to the data collection conditions or the processing conditions related to the analysis before the analysis of the intended specimen is executed.

That is, to solve the above-mentioned problems, the present invention provides a chromatographic analyzer for subjecting specimen components, which are temporally separated by a column according to a predetermined separation condition, to one of detection under a predetermined data collection condition for collection of detected data, and processing under a predetermined processing condition, one of the data collection condition and the processing condition including a temporal parameter related to an elapsed time from a specimen introduction time point to the column, the chromatographic analyzer including: (a) condition storing means for storing one of the data collection condition and the processing condition which are set by an operator with respect to an analysis of an intended specimen; (b) actual measurement value acquiring means for acquiring a retention time of a known given component on the basis of a chromatograph that is an analysis result obtained by executing an analysis of a standard specimen including the given component under a separation condition where the analysis of the intended specimen is to be executed; and (c) correcting means for correcting the temporal parameter included in the one of the data collection condition and the processing condition, which is stored in the condition storing means, by using the retention time acquired by the actual measurement value acquiring means, in which the analysis of the intended specimen is executed in a state where the temporal parameter included in the data collecting condition or the processing condition is corrected by the correcting means.

According to a representative aspect of the present invention, there is provided a chromatographic analyzer, in which: the chromatographic analyzer is a gas chromatograph mass spectrometer or a liquid chromatograph mass spectrometer including a mass spectrometer for detecting the specimen components which are temporally separated by the column; and the temporal parameter included in the data collection condition determines a measurement time range for a case of conducting one of the scanning measurement and the selected ion monitoring measurement in the mass spectrometer.

In this specification, "separation conditions" are a part of analysis conditions, which are conditions that influence the separation of the specimen component in the column, more specifically, the kind of column, the size (i.e., length or inner diameter) of the column, the column temperature (rising temperature program), or the movement speed of a mobile phase.

In the chromatographic analyzer according to the present invention, a standard specimen including a known given component is analyzed under the same separation conditions as those of the analysis of an intended specimen before the intended specimen is analyzed, to thereby acquire the chromatogram. In a case of the chromatograph mass spectrometer, the chromatogram may be one of a total ion chromatogram intended for all of ions and a mass chromatogram focusing on the mass number of a given component. Since the peak of the given component appears in the obtained chromatogram, the actual measurement value acquiring means obtains the retention time of the given component from the position of the peak. The correcting means corrects the temporal parameter that is contained in the data collection conditions or the processing conditions which are stored in the condition storing means by using the actual measurement value of the retention time. In this situation, the chromatographic analyzer is capable of adopting any one of two methods.

One of those methods is based on the retention time of the given component when the standard specimen is analyzed under the analysis conditions on the basis of which the data collection conditions or the processing conditions which are stored in the condition storing means are set. The retention time of the given component is varied depending on a difference of the analysis conditions from the standard time. Since it can be assumed that the retention times of other various components other than the given component are also varied with the same tendency, it is possible to correct the temporal parameter that is included in the data collection conditions or the processing conditions.

The other method is a method of using a retention index of an intended component. As known, the retention index is a relative value having, for example, a congener series of n-alkane as a reference material, and does not depend on the analysis conditions such as a mobile phase (for example, carrier gas) flow rate or a column temperature, which is different from the retention time. Therefore, when the retention index of the intended component is known, the reference material is analyzed as the given component to acquire the retention time, and a variation of the retention time of the intended component is estimated from the actual measurement value of the retention time and the retention index of the intended component, thereby making it possible to correct the temporal parameter that is included in the data collection conditions and the processing conditions.

In any event, the temporal parameter that is included in the data collection conditions or the processing conditions which are corrected by the correcting means reflects the separation characteristic of the column at the time, that is, at a time point where the intended specimen is to be analyzed. Therefore, the analysis of the intended specimen is executed to collect the detected data or to perform given processing, thereby making it possible to obtain an appropriate result that is intended by an operator.

As described above, according to the chromatographic analyzer of the present invention, even in the case where a large number of temporal parameters are contained in the data collection conditions or the processing conditions, the operation of individually changing the parameters by the operator is not required. As a result, it is possible to reduce the load on the operator and prevent an error such as an input error which is accompanied by the changing operation. In particular, a remarkable improvement in the operation efficiency can be expected by using the chromatographic analyzer of the present invention, for example, in the case where the number of ion sets in the SIM measurement of the GC/MS is large, in the case where there is required complicated parameter setting in a measurement mode where the SIM measurement and the scanning measurement are conducted at the same time, or in the case where there is required the complicated parameter setting in the MS/MS measurement.

BRIEF DESCRIPTION OF THE DRAWINGS

In the accompanying drawings:

FIG. 4 is a diagram for explaining a correcting process of an SIM measurement parameter in the GC/S according to the embodiment; and FIG. 5 is a diagram for explaining another correcting process of an SIM measurement parameter in the GC/MS according to the embodiment.

DETAILED DESCRIPTION OF THE EMBODIMENTS

First, a description will be given of a method of correcting a temporal parameter that is included in data collection conditions or processing conditions in a chromatographic analyzer according to the present invention. The correction of the temporal parameter is based on a process of estimating a retention time of a peak of an intended component after separation conditions are changed, on the basis of the retention time of the peak of the intended component before the separation conditions are changed. As the processing method, there are two methods stated below:

Method I is a method of estimating the retention time of the peak of an intended component on the basis of an actual measurement value of the retention time of a reference component for correction; and Method II is a method of estimating the retention time of the peak of an intended component on the basis of the information on the retention index of the intended component.

Figure 2A:
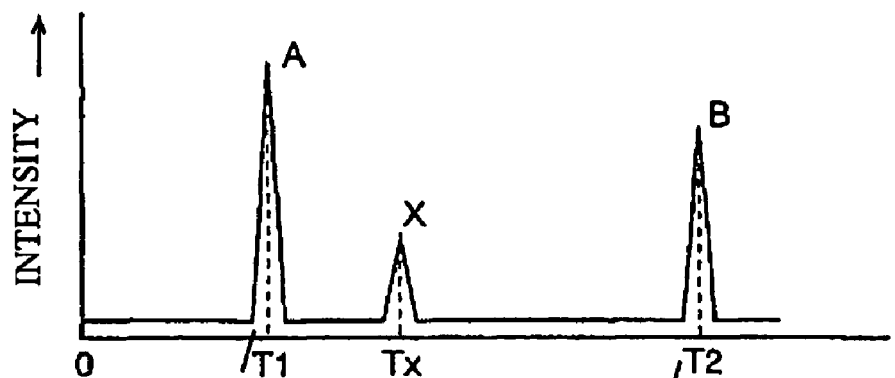
FIGS. 2A and 2B are diagrams each showing an example of a chromatogram for explaining a method of correcting a temporal parameter in the present invention.
Figure 2B:
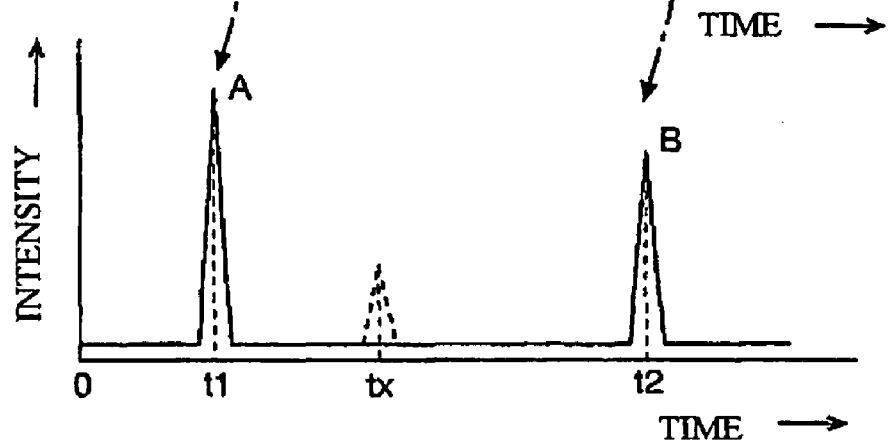

First, the method I will be described. A chromatogram (i.e., total ion chromatogram in the GC/MS) which is obtained by the analysis under certain separation conditions (hereinafter, referred to as separation conditions F1) is shown in FIG. 2A. Peaks A and B that appear in the chromatogram are peaks of the reference component for correction, and a peak X that is temporally interposed between those two peaks A and B is a peak of the intended component to be originally analyzed. In a case where, for example, the inlet end of the column is cut off as a change of the separation conditions from a time point where the analysis is executed, the column length is shortened by the cutoff length, so the passage of the respective components that are introduced in the column is made earlier than that before the column is cut off. It is assumed that a standard specimen for correction is analyzed under the separation conditions (hereinafter, referred to as separation conditions F2) after the column has been cut off, and the chromatogram shown in FIG. 2B is obtained.

The calculation expression for estimating the retention time of the peak of the intended component when changing from the analysis under the separation conditions F1 to the analysis under the separation conditions F2 is represented by the following expression (1).

$$tx=(Tx-T1)/(T2-T1) \times (t2-t1)+t1 \quad (1)$$

where tx indicates an estimated value of the retention time of the peak X of the intended component, t1 indicates an actual measurement value of the retention time of a first reference component under the separation conditions F2, t2 indicates an actual measurement value of the retention time of a second reference component under the separation conditions F2, Tx indicates a retention time of an intended component peak under the separation conditions F1, T1 indicates a retention time of a first reference component under the separation conditions F1, and T2 indicates a retention time of a second reference component under the separation conditions F1. All of the above items are shown in FIGS. 2A and 2B. As a result, since the retention time of the peak of the intended component after the separation conditions have been changed is substantially obtained, it is possible to correct the temporal parameter for detecting the data related to the intended component peak or processing the intended component based on the obtained retention time.

Figure 3:
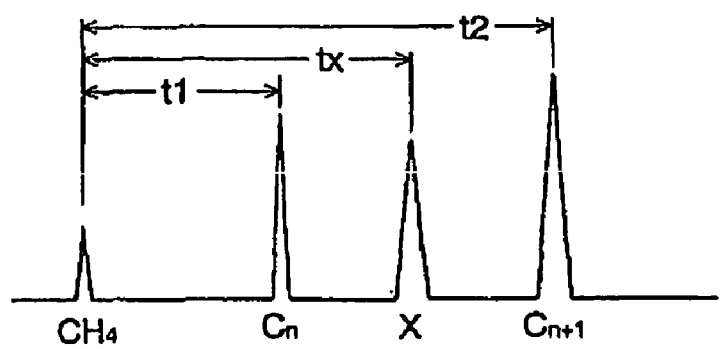
FIG. 3 is a diagram showing an example of a chromatograph for explaining another method of correcting a temporal parameter in the present invention.

Subsequently, the method II will be described. In this example, let us consider the retention index in a case where a congener series of n-alkane, which is the most typical, is a reference material. It is assumed that the peak of a material X exists between the adjacent peaks Cn and Cn+1 of n-alkane on the basis of the appearance position of the peak of methane ($CH_4$) whose carbon number n is 1 in the chromatogram shown in FIG. 3. In the case of the temperature rising analysis, the retention index Ix of the intended component X is defined by the following expression (2).

$$Ix=[(tx-tc1)/(tc2-tc1)] \times 100+100 \times n \quad (2)$$

where Tx indicates a retention time of an intended component peak, tc1 indicates a retention time of the peak of n-alkane whose carbon number is n, and tc2 indicates a retention time of the peak of n-alkane whose carbon number is n+1. The retention index does not depend on the size of the column or the mobile phase velocity. Therefore, when the retention index Ix of the intended component is known, it is possible to estimate the retention time of the peak of the intended component under the separation conditions F2 through the modification of Expression (2), or Expression (3).

$$tx=(Ix/100-n) \times (t2-t1)+t1 \quad (3)$$

where tx indicates an estimated value of the retention time of the peak X of the intended component, t1 indicates an actual measurement value of the retention time of the peak of Cn under the separation conditions F2, and t2 indicates an actual measurement value of the retention time of the peak of Cn+1 under the separation conditions F2.

As a result, since the retention time of the peak of the intended component after the separation conditions are changed is substantially obtained as in the method I, it is possible to correct the temporal parameter for detecting data related to the intended component peak or processing the intended component based on the retention time.

Figure 1:
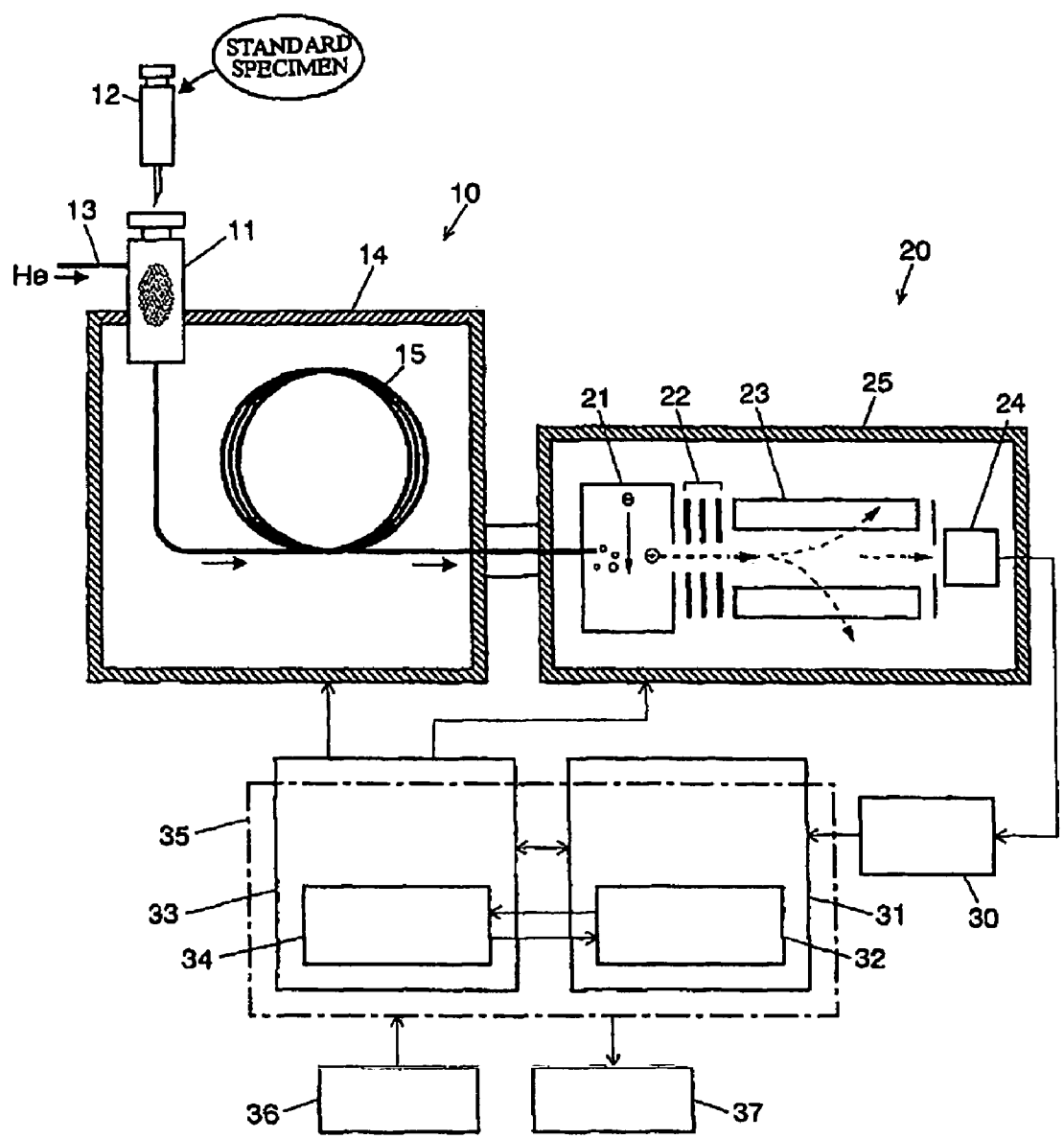
FIG. 1 is a block structural diagram showing a main portion of a GC/MS according to an embodiment of the present invention.

Now, a description will be given of GC/MS of a chromatographic analyzer according to an embodiment of the present invention with reference to the accompanying drawings. FIG. 1 is a block structural diagram showing the main portion of the GC/MS according to this embodiment.

In a GC section 10, a specimen gasifying chamber 11 is disposed at an inlet of a column 15 that is heated at an appropriated temperature by means of a column oven 14, and a carrier gas (typically He gas) is supplied to the specimen gasifying chamber 11 through a carrier gas flow path 13 at a given flow rate, and then flows into the column 15. In this situation, when a small amount of liquid specimen is injected into the specimen gasifying chamber 11 by means of a micro syringe 12, the liquid specimen is gasified promptly and then sent to the interior of the column 15 together with a carrier gas flow. The respective components in the specimen gas is temporally separated while passing through the column 15, and then reaches an outlet of the column 15, and is introduced into an ionizing chamber 21 of an MS section 20.

In the MS section 20, the ionizing chamber 21, an ion optical system 22, a quadrupole mass filter 23, and a detector 24 are disposed within a vacuum chamber 25 that conducts vacuum suction by the aid of a vacuum pump (not shown). As described above, the specimen molecules or atoms that have been sequentially introduced into the ionizing chamber 21 with a progress of the GC analysis are ionized by coming into contact with, for example, a thermoelectron. The generated ions are extracted from the outside of the ionizing chamber 21, converged by the ion optical system 22, and introduced into a space in a longitudinal axial direction of the quadrupole mass filter 23 that is composed of four rod electrodes. A voltage that superimposes a DC voltage on a high frequency voltage is applied to the quadrupole mass filter 23, and only ions having the mass number (i.e., mass/electric charge) corresponding to the applied voltage pass through the space in the longitudinal axial direction, reaches the detector 24, and are detected.

A detection signal from the detector 24 is converted into digital data by means of an A/D converter 30, and then sent to a data processing section 31. The data processing section 31 conducts a given arithmetic processing to appropriately produce a mass spectrum, a mass chromatogram, a total ion chromatogram, or the like and executes a quantitative analysis or a qualitative analysis on the basis of a given algorithm. The operation of the respective blocks that constitute the GC section 10 and the MS section 20 is fully controlled by a control section 33. The control section 33 and the data processing section 31 execute a given control/processing program on a personal computer 35 that is equipped with an operation section 36 and a display section 37, to thereby achieve the respective functions.

In the GC/MS according to this embodiment, as characteristic configurations, an analysis condition information storing section 34 is disposed in the control section 33, and an analysis condition change processing section 32 having a function of correcting the information contents of an analysis condition information storing section 34 is disposed in the data processing section 31. In other words, the analysis condition information storing section 34 is memory means for storing all of various conditions required to implement the GC/MS analysis such as SIM measurement parameters which are the separation conditions or the data collection conditions which affect the separation characteristics in the column described above. Also, the analysis condition change processing section 32 corrects the data collection conditions that are stored in the analysis condition information storing section 34 on the basis of the above method.

It is assumed that the SIM measurement parameter shown in FIG. 4 is set as the data collection conditions under the certain separation conditions F1 by the operator. That is, three ion sets having different designated measurement mass numbers, respectively, are set. In a case of conducting the analysis under the separation conditions F1, the MS section 20 may conduct the SIM measurement according to the SIM measurement parameters to collect the detected data. However, in a case of cutting off the inlet end of the column, or in a case of changing the separation conditions such as the temperature rising program, it is necessary to change all of the measurement start times and the measurement end times of the respective ion sets of the SIM measurement parameter because the chromatogram is moved in the time axial direction as described above.

In this situation, the operator instructs the correcting process of the parameter through the operation section 36. Upon receiving the instruction, the control section 33 first executes the GC/MS analysis of a given standard specimen for correction under the changed separation conditions F2. In this case, since it is necessary to acquire the total ion chromatogram, the scanning measurement in a given mass number range is automatically set. Because a plurality of reference components are contained in the standard specimen, the chromatogram in which the peaks of those reference components appear is produced as the analysis result in the data processing section 31. After that, the chromatogram is subjected to the peak detection, and the respective peaks are identified, to thereby obtain the actual measurement value of the retention time of the reference component.

Subsequently, the SIM measurement parameters that are stored in the analysis condition information storing section 34 are subjected to the correction processing. More specifically, it is assumed that the measurement start time of the ion set in the N-th line of the table shown in FIG. 4 is Ts[N] and the measurement end time is Te[N], and the respective times are calculated as Tx in Expression (1), and it is assumed that the values of tx to be obtained are the measurement start time Ts'[N] after the correction and the measurement end time Te'[N] after the correction. In other words, in a case where the measurement start time and the measurement end time of the ion set in the N-th line are interposed between the retention time of the first reference component and the retention time of the second reference component, the respective values are calculated on the basis of the following expressions (4) and (5).

$$Ts'[N]=(Ts[N]-T1)/(T2-T1)\times(t2-t1)+t1 \ldots \quad (4)$$

$$Te'[N]=(Te[N]-T1)/(T2-T1)\times(t2-t1)+t1 \ldots \quad (5)$$

where Ts'[N] indicates a corrected value of the measurement start time of the ion set in the N-th line, Te'[N] indicates a corrected value of the measurement end time of the ion set in the N-th line, t1 indicates an actual measurement value of the retention time of the first reference component, t2 indicates an actual measurement value of the retention time of the second reference component, Ts[N] indicates a set value of the measurement start time of the ion set in the N-th line (i.e., a value shown in FIG. 4), Te[N] indicates a set value of the measurement end time of the ion set in the N-th line (i.e., a value shown in FIG. 4), T1 indicates a retention time of the first reference component under the separation conditions F1, and T2 indicates a retention time of the second reference component under the separation conditions F1.

The ion sets of all the lines are subjected to the same calculation on the basis of the retention time information of the reference component for correction in each of the ion sets, to thereby calculate the measurement start time and the measurement end time and to correct the respective values as shown in FIG. 5. Sequentially, when the GC/MS analysis of the intended specimen is executed, the measurement mass number is switched over in each of the measurement time ranges according to the corrected SIM measurement parameter, to thereby produce, for example, the mass chromatogram in each of the measurement mass numbers. In this example, there are three ion sets, but in the actual device, the number of ion sets is much larger than three in many cases, and all of the SIM measurement parameters are automatically appropriately corrected according to the separation conditions for analyzing the intended specimen through the above processing, to thereby remarkably reduce work load on the operator.

In the above description, the correction processing is conducted according to the method I, but the correction processing may be conducted according to the method II. In this case, the retention index values Is[N] and Ie[N] corresponding to the respective measurement start time Ts[N] and the measurement end time Te[N] are obtained from the relationship between the measurement start time Ts[N] and the measurement end time Te[N] of the ion set in the N-th line shown in FIG. 4, and the retention time of the n-alkane under the separation condition F1 in advance. Then, the standard specimen of n-alkane is analyzed also after the conditions are changed to the separation conditions F2 to produce the total ion chromatogram, and the peaks corresponding to the respective carbon numbers are detected to obtain the actual measurement values of the respective retention times.

Then, in a case where the measurement start time and the measurement end time of the ion set in the N-th line are interposed between the retention time of the first reference component and the retention time of the second reference component, the corrected values of the measurement start time and the measurement end time are calculated from the following expressions (6) and (7) based on Expression (3).

$$Ts'[N] = (Is[N]/100 - n) \times (t2 - t1) + t1 \ldots \quad (6)$$

$$Te'[N] = (Ie[N]/100 - n) \times (t2 - t1) + t1 \ldots \quad (7)$$

where t1 indicates an actual measurement value of the retention time of Cn under the separation condition F2, and t2 indicates an actual measurement value of the retention time of Cn+1 under the separation condition F2.

Even with the above processing, all of the SIM measurement parameters can be automatically corrected as in the above case, and the SIM measurement can be executed on the basis of the corrected value.

In the above embodiment, a description is given of a case in which the temporal parameters among the SIM measurement parameters, that is, the measurement start time and the measurement end time of the respective ion sets are corrected. Similarly, not the SIM measurement parameter but the scanning measurement parameter can be corrected. Also, the above processing can be used to correct various temporal parameters which are set in the measurement mode in which the scanning measurement and the SIM measurement are executed at the same time, or the MS/MS analysis mode.

In addition, it is easily conceivable that the present invention can be applied to a case in which the data correction or the processing of the separated specimens is executed according to the temporal parameter that is set by the operator in advance, not in the chromatograph mass spectrometer such as the GC/MS or the LC/MS, but in various chromatographic analyzer such as the GC or LC using another detector such as an ultraviolet-visible spectrophotometer, or an LC fractionation apparatus that is combined with a fractionation device.

What is claimed is:

1. A method for subjecting specimen components which are temporally separated by a column according to a predetermined separation condition, to one of detection under a predetermined data collection condition for collection of detected data, and processing under a predetermined processing condition, one of the data collection condition and the processing condition including a temporal parameter related to an elapsed time from a specimen introduction time point to the column, the method comprising:

(a) storing one of the data collection condition and the processing condition which are set by an operator with respect to an analysis of an intended specimen;

(b) acquiring a retention time of a known given component on the basis of a chromatogram that is an analysis result obtained by executing an analysis of a standard specimen including the given component under a separation condition where the analysis of the intended specimen is to be executed;

(c) correcting the temporal parameter included in the one of the data collection condition and the processing condition, which is stored in the condition storing means, by using the retention time acquired by the actual measurement value acquiring means, and (d) analyzing the intended specimen in a state where the temporal parameter included in the data collecting condition or the processing condition has been corrected by the correcting means.

* * * * *